United States Patent [19]
Tankovich

[11] Patent Number: 5,713,845
[45] Date of Patent: *Feb. 3, 1998

[54] LASER ASSISTED DRUG DELIVERY

[75] Inventor: Nikolai Tankovich, San Diego, Calif.

[73] Assignee: ThermoLase Corporation, San Diego, Calif.

[*] Notice: The term of this patent shall not extend beyond the expiration date of Pat. No. 5,423,803.

[21] Appl. No.: 489,352

[22] Filed: Jun. 12, 1995

Related U.S. Application Data

[63] Continuation-in-part of Ser. No. 280,928, Jul. 26, 1994, abandoned, Ser. No. 257,021, Jun. 8, 1994, Pat. No. 5,423,803, and Ser. No. 5,810, Jan. 19, 1993, Pat. No. 5,425,728, which is a continuation-in-part of Ser. No. 783,789, Oct. 29, 1991, Pat. No. 5,226,907.

[51] Int. Cl.$^6$ .............................. A61N 1/30; A61B 17/36
[52] U.S. Cl. .................................................. 604/20; 606/9
[58] Field of Search ...................... 128/898; 601/2; 604/20, 22, 49, 290; 606/1, 9, 131–133; 607/88–90

[56] References Cited

U.S. PATENT DOCUMENTS

| | | |
|---|---|---|
| 3,538,919 | 11/1970 | Mayer . |
| 3,693,623 | 9/1972 | Harte et al. . |
| 3,769,963 | 11/1973 | Goldman et al. . |
| 3,794,028 | 2/1974 | Mueller et al. . |
| 3,834,391 | 9/1974 | Block . |
| 3,900,034 | 8/1975 | Katz et al. . |
| 4,336,809 | 6/1982 | Clark . |
| 4,388,924 | 6/1983 | Weissman et al. . |
| 4,461,294 | 7/1984 | Baron . |
| 4,608,978 | 9/1986 | Rohr . |
| 4,617,926 | 10/1986 | Sutton . |
| 4,712,543 | 12/1987 | Baron . |
| 4,813,412 | 3/1989 | Yamazaki . |
| 5,059,192 | 10/1991 | Zaias . |
| 5,423,803 | 6/1995 | Tankovich et al. ................. 606/9 |

FOREIGN PATENT DOCUMENTS

| | | |
|---|---|---|
| 1041610 | 6/1974 | Canada . |
| 1208702 | 7/1986 | Canada . |
| 64967A2 | 4/1995 | European Pat. Off. . |
| 2267122 | 11/1975 | France . |
| 2590791 | 6/1987 | France . |
| 2595239 | 9/1987 | France . |
| 2515697 | 10/1975 | Germany . |
| 3220962 | 12/1983 | Germany . |
| 63-2495 | of 1977 | Japan . |
| 8002640 | 12/1980 | WIPO . |
| 8602783 | 5/1986 | WIPO . |
| 9104073 | 4/1991 | WIPO . |
| WO91/13653 | 9/1991 | WIPO . |
| WO93/21992 | 11/1993 | WIPO . |

OTHER PUBLICATIONS

Porphyrins in Tumor Phototherapy—Andereoni, May 16, 1983 1984—pp. 143–155.

Investigation and Therapy in Dermatology A. Anders, et al—Conf. Laser 77 Optics–Electronics (20–24 Jun. 1977).

*Primary Examiner*—Glenn K. Dawson
*Attorney, Agent, or Firm*—Fish & Richardson P.C.

[57] ABSTRACT

The present invention provides a process for laser assisted drug delivery through the skin. A drug and a explosive absorber of light energy are applied topically to the skin. The treated area of the skin is illuminated with very short pulses of light which is preferentially absorbed by the absorber causing a very large number of tiny explosions. The tiny explosion forces portions of the drug to penetrate into the skin. A preferred embodiment utilizes small graphite particles and an Nd:YAG short pulse laser.

33 Claims, 2 Drawing Sheets

LASER ASSISTED DRUG DELIVERY

This is a continuation in part of Ser. No. 08/280,928 filed Jul. 26, 1994, abandoned, Ser. No. 08/257,021 filed on Jun. 8, 1994 now U.S. Pat. No. 5,423,803 and Ser. No. 08/005, 810 filed Jan. 19, 1993, now U.S. Pat. No. 5,425,728 which was a continuation in part of Ser. No. 07/783,789 filed Oct. 29, 1991, now U.S. Pat. No. 5,226,907 issued Jul. 13, 1993. This invention relates to processes and equipment for drug delivery skin treatment and in particular equipment and procedures for delivering drugs through skin to such processes which utilize lasers.

BACKGROUND OF THE INVENTION

A section of human skin showing a cross section of one hair is shown in FIG. 1. FIG. 1 shows the hair shaft 33 of a hair growing in a hair duct 31, from dermal papilla 32, a nerve ending 34, a sweat gland 35 a sebaceous gland 38, arteries 36 and veins 37.

The epidermis, 39 in FIG. 1, of the human skin comprises several distinct layers of skin tissue. The deepest layer is the stratum basale layer which consists of columnar cells. The next layer up is the stratum spinosum composed of polyhedral cells. Cells pushed up from the stratum spinosum are flattened and synthesize keratohyalin granules to form the stratum granulosum layer. As these cells move outward they lose their nuclei and the keratohyalin granules fuse and mingle with tonofibrils. This forms a clear layer called the stratum lucidum. The cells of the stratum lucidum are closely packed. As the cells move up from the stratum lucidum they become compressed into many layers of opaque squamas. These flattened cells have become completely filled with keratin and have lost all other internal structure, including nuclei. These squamas constitute the outer layer of the epidermis, the stratum corneum. At the bottom of the stratum corneum the cells are closely compacted and adhere to one another strongly, but higher in the stratum they become loosely packed and eventually flake away at the surface. Also shown in FIG. I is hair stem 33 sebaceous gland 38, hair duct 31, nerve ending 34, veins and arteries 36 and 37, sweat gland 35 and pupilla 32.

There exists many prior art methods for drug delivery through the skin. These include injection with a hypodermic needle, high pressure injectors, electrophoresis techniques, sonophoresis techniques and dermo patches. A laser assisted method of drug delivery has recently been proposed in which a laser is used to evaporate tiny holes in an area of the skin afterwhich a drug is applied to the treated area. It is known that infiltration of drugs through the skin can be increased by forcing the drug into hair follicles.

It is known that graphite vaporizes at about 3,600° C. It is known that graphite is a strong absorber of infrared light and that infrared light such as the 1.06 micron laser beam produced by the Nd:YAG laser will penetrate several millimeters through human skin.

What is needed is a simple quick treatment process for drug delivery through the skin.

SUMMARY OF THE INVENTION

The present invention provides a process for laser assisted drug delivery through the skin. A drug and an explosive absorber of light energy are applied topically to the skin. The treated area of the skin is illuminated with very short pulses of light which is preferentially absorbed by the absorber causing a very large number of tiny explosions. The tiny explosion forces portions of the drug to penetrate into the skin. A preferred embodiment utilizes small graphite particles and an Nd:YAG short pulse laser.

DETAILED DESCRIPTION OF PREFERRED EMBODIMENTS

Figure 1:
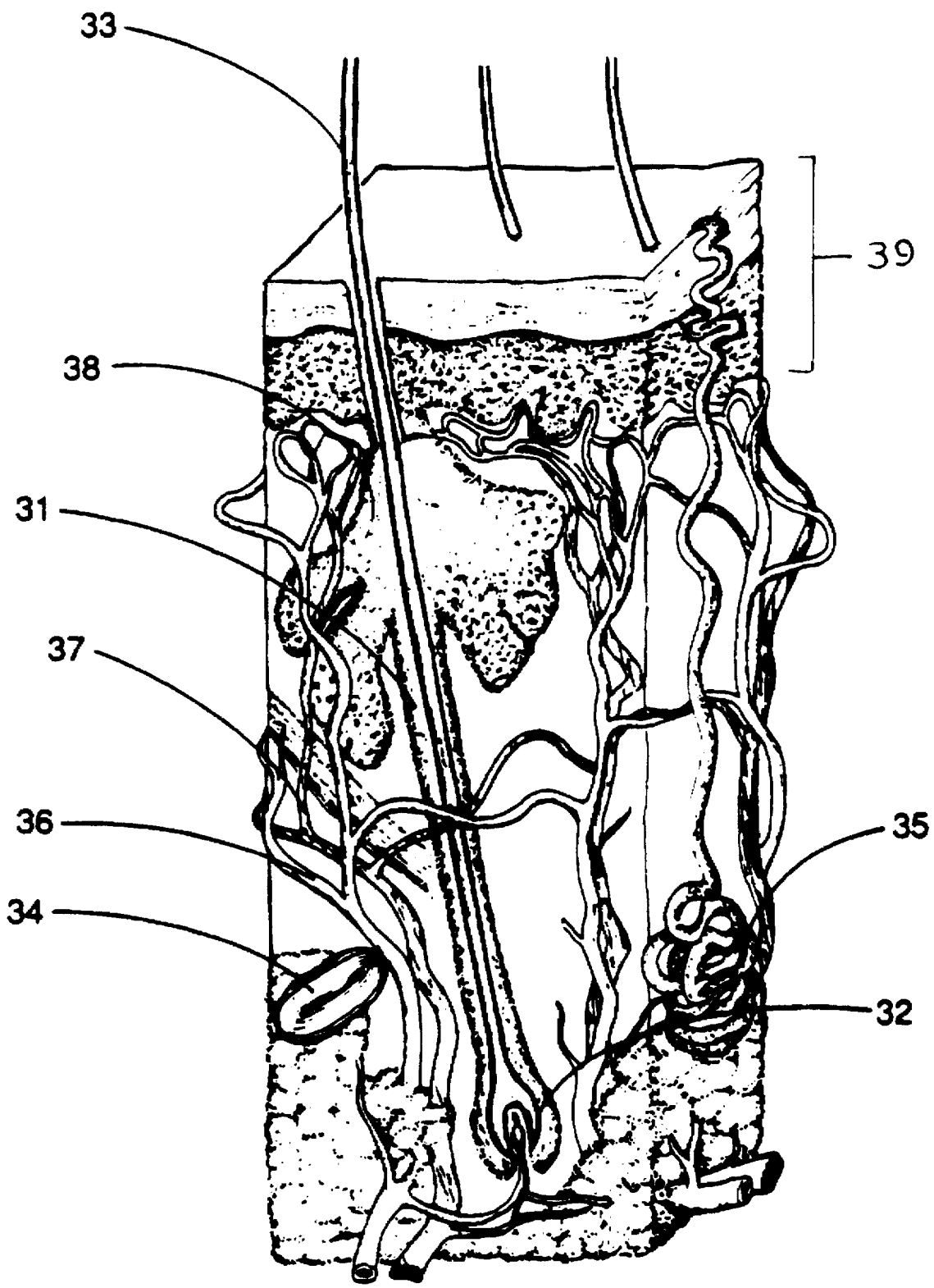
FIG. 1 shows a skin section.
Figure 2:
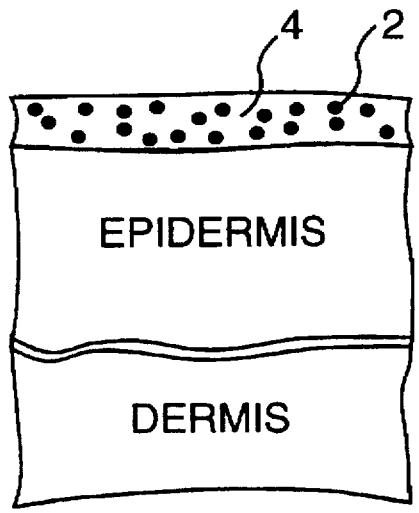
FIGS. 2–5 demonstrate four embodiments of the present invention.

Applicant has discovered that when small particles of graphite are illuminated with very short pulses of laser light of sufficient energy the individual particles explode violently. If the pulse-duration and energy is chosen correctly carbon particles in the 1 micron size range will violently break apart into smaller fragments. Subsequent pulses continue to break the particles into even smaller sizes until the particles disappear. For example, in an inert atmosphere after repeated illumination with 1.06 micron, 12 nanosecond, 3 Joules per $cm^2$ pulses, the particles are broken into extremely small particles bearly visible to the unaided eye. But in air the particles after such repeated illumination disappear completely, apparently forming $CO_2$.

The present invention utilizes the explosive force created by the partial or complete vaporization of small particles in very short time intervals in order to force drugs into the body through skin tissue.

FIRST EMBODIMENT

Carbon particles— Nd:YAG Laser— Drug

Our basic preferred process can be explained as follows. We utilize an Nd:YAG laser producing 12 nanosecond laser pulses at 1.06 microns with an energy per pulse of about 1.5 Joule and a laser cross section of about 0.5 $cm^2$ to produce a beam of about 3 Joules per $cm^2$. A mixture of the drug to be delivered and small graphite particles is prepared. We prefer particles having dimensions of about 1 micron. The mixture is applied topically to the skin and rubbed into it so that portions of the mixture is infiltrated into spaces in the skin. These spaces include small cracks in the epidermis areas in a around sebaceous glands. The treated section of the skin is then illuminated with the pulse beams described above.

Graphite is very absorptive of laser energy at the 1.06 μm wavelength. The latent heat of vaporization is about $10^5$ $J/cm^3$ for cold solid graphite. (The energy required to heat room temperature graphite to the sublimination temperature is roughly 4% of the sublimination energy.) Thus, to vaporize a 1 micron cube ($10^{-12}cm^3$) would require approximately $10^{-7}$J. The energy falling on the surface of the 1 micron particle ($1\times10^{-8}cm^2$) in a 3J/$cm^2$ pulse is $3 \times 10^{-8}$J, about one third of the energy needed to totally vaporize the particle. Therefore, a significant portion of the particle is vaporized. The energy is deposited in a few nanoseconds so there is no time for the heat to diffuse; therefore, the particle explodes violently upon being illuminated by the pulse. (Subsequent pulses will vaporize the smaller particles created by the earlier pulses.) The resulting forces of the tiny explosions forces a portion of the drug into the skin tissue where it is absorbed into the body.

Drug List

The following are drugs which could be applied using the process described above.

Drugs (in the form of ointment and liquid solution or emulsion) to be delivered transcutaneously by the laser forcing method:

Antibiotics: Bacitracin-Neomycin-Polyxin B

Antibacterial: Mycostatin

Hormones: Hydrocortisone

Vasodilators: Minoxidil

Chemotherapuetic Drugs: Adriamycin

Anesthetics: Lidocaine

Immunomodulators: Intron A

PDT Sensitizers: ALA, HPD, Photophrin

Anticoagulants: Heparin

Nitrites: Nitroglycerin

Enzymes: Streptase

Deposition Forms: Liposomes, Magnetic Fluid Drugs, Coacervates

Radio Isotopes: Be, Cd

In all cases our preferred treatment is to mix these drugs directly with one micron graphite particles at a weight ratio of about 20% carbon to 80% drug.

ENHANCEMENTS

The following are techniques for enhancing the effects of the above process.

Figure 5:
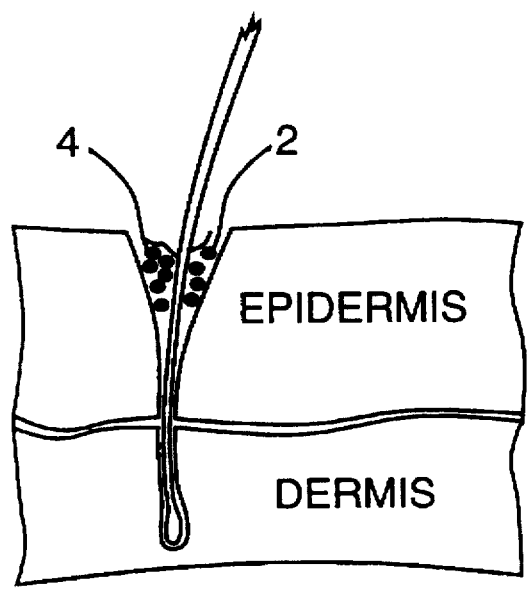

One method of enhancement is to infiltrate the graphite drug mixture into hair follicles prior to illumination as shown in FIG. 5. The graphite particles are 2 and the drug 4. The walls of the follicles are much thinner than the epidermis so entry in the dermis portion of the skin is greatly enhanced upon illumination.

Figure 3:
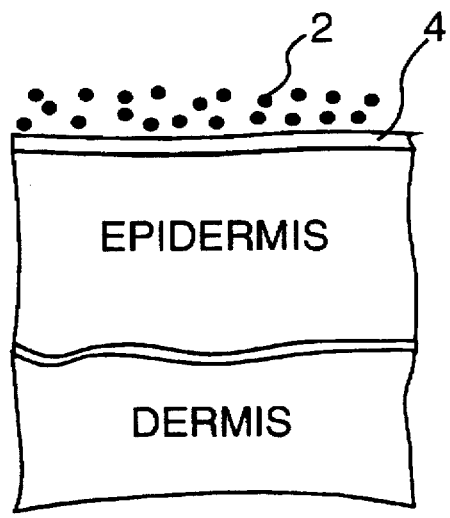

A transparent tape can be applied over the graphite drug mixture shown in FIG. 3 prior to illumination.

A glass cover such as a microscope slide can be applied with about 1 psi pressure during illumination to enhance shock waves caused by the drug explosions. The glass could be a part of an articulated arm delivering the laser beam.

OTHER EMBODIMENTS

Figure 4:
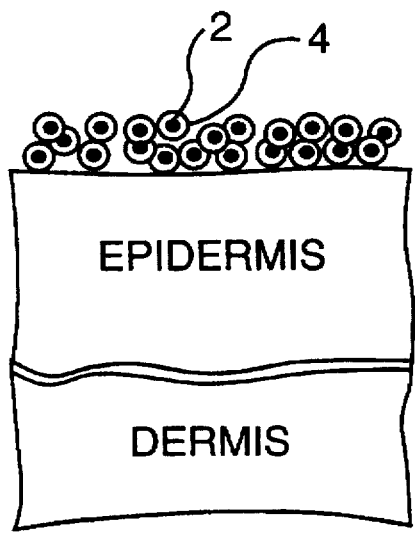

Persons skilled in the laser medicine art will recognize that there are a great many ways to practice this invention other than the few described above. Many particles in addition to graphite will explode upon illumination with short laser pulses. Particles chosen, however, must have a high absorption at the wavelength of the laser chosen. There are many short pulse lasers other than the Nd:YAG laser which could be utilized. Again a match with the particles must be assured. As an alternate to mixing the particles and the drug; the drug could first be applied to the skin in a layer and a second layer of graphite particles could be applied over the drug layer as shown in FIG. 3. The particles could be coated individually with a drug as shown in FIG. 4.

Thus, the reader should not construe the above examples as limitations on the scope of the invention, but merely as exemplifications of preferred embodiments thereof. Those skilled in the art will envision many other possible variations are within its scope. Accordingly the reader is requested to determine the scope of the invention by the appended claims and their legal equivalents, and not by the examples which have been given.

We claim:

1. A process for transdermal drug delivery comprising the steps of:
   (a) topically applying to a section of skin a drug and an explosive absorber, said absorber having a high absorption at at least one frequency band of light,
   (b) illuminating said section of skin with pulses of said at least one frequency band of light, so as to impart to the absorber sufficient energy to cause at least a portion of said absorber to explode with the resulting explosion forcing at least a portion of said drug into said skin transdermally.

2. A process as in claim 1 wherein said absorber comprises a plurality of carbon particles.

3. A process as in claim 2 wherein said carbon particles are graphite particles having dimensions of about 1 micron.

4. A process as in claim 2 wherein said carbon particles have a dimension of about of about 1 micron.

5. A process as in claim 2 wherein said pulses are pulses from a Nd:YAG laser.

6. A process as in claim 5 wherein said at least one frequency band of light has a wavelength of about 1.06 microns.

7. A process as in claim 5 wherein said pulses define a pulse duration and the pulse duration is about 12 nanoseconds.

8. A process as in claim 5 wherein the energy of the pulses is about 3 Joules/$cm_2$.

9. A process as in claim 2 wherein said pulses are pulses from a $CO_2$ laser.

10. A process as in claim 5 or 8 wherein the beam of the laser has a cross section of about 0.5 $cm_2$.

11. A process as in claim 1 wherein a confinement means, transparent to said at least one frequency band of light is placed firmly over said topically applied drug and absorber for the duration of said forcing explosion for the purpose of confining said forcing explosion.

12. A process as in claim 1, and further comprising the additional step of forcing said drug and absorber into spaces in said skin section prior to illumination.

13. A process as in claim 11 wherein said spaces comprise hair ducts.

14. A process as in claim 12 wherein said spaces in said skin comprises spaces between superficial epidermal skin cells.

15. A process as in claim 12 wherein said spaces in said skin comprises spaces within sebaceous glands.

16. A process as in claim 12 wherein said spaces in said skin comprise spaces adjacent to sebaceous glands.

17. A process as in claim 1 wherein the drag and the absorber are in combination and the weight ratio of the absorber to the drug is about 1:4.

18. A process as in claim 17 wherein the combination is a mixture.

19. A process as in claim 17 wherein the drug coats the absorber.

20. A process as in claim 1 wherein the drug is selected from the group consisting of an antibiotic, an antibacterial, a hormone, a vasodilator, a chemotherapeutic, an anesthetic, an immunomodulator, a PDT sensitizer, an anticoagulant, a nitrite, an enzyme, a radio isotope, and a deposition form.

21. The process as in claim 20 wherein the antibiotic is selected from the group consisting of Bacitracin, Neomycin and PolysinB, and mixtures thereof.

22. The process as in claim 20 wherein the antibacterial is mycostatin.

23. The process as in claim 20 wherein the hormone is hydrocortisone.

24. The process as in claim 20 wherein the vasodilator is minoxidil.

25. The process as in claim 20 wherein the chemotherapeutic is adriamycin.

26. The process as in claim 20 wherein the anesthetic is lidocaine.

27. The process as in claim 20 wherein the immunomodulator is intron A.

28. The process as in claim 20 wherein the PDT sensitizer is selected from the group consisting of ALA, HPD and photophrin, and mixtures thereof.

29. The process as in claim 20 wherein the anticoagulant is heparin.

30. The process as in claim 20 wherein the nitrite is nitroglycerin.

31. The process as in claim 20 wherein the enzyme is streptase.

32. The process as in claim 20 wherein the deposition form is selected from the group consisting of a liposome, a magnetic fluid drug, and a coacervate.

33. The process as in claim 20 wherein the radio isotope is selected from the group consisting of Be and Cd, and mixtures thereof.

* * * * *